United States Patent
Medeiros Junior et al.

(10) Patent No.: US 12,379,364 B2
(45) Date of Patent: Aug. 5, 2025

(54) METHOD FOR DETERMINING THE COMPOSITION OF WATER IN LOW BSW OILS

(71) Applicant: Petróleo Brasileiro S.A.—Petrobras, Rio de Janeiro (BR)

(72) Inventors: Iris Medeiros Junior, Rio de Janeiro (BR); Ricardo Augusto Pereira De Avila, Rio de Janeiro (BR); Rogerio Mesquita De Carvalho, Rio de Janeiro (BR); Rainerio Escalfoni Junior, Rio de Janeiro (BR); Ana Gabriela Apolonio De Souza, Rio de Janeiro (BR); Oto Leonardo Reis Gomes, Rio de Janeiro (BR); Roberta De Moraes Maciel, Rio de Janeiro (BR); Alessandra Rangel Cassella, Rio de Janeiro (BR); Elisangela Fragoso Reis Da Rocha, Rio de Janeiro (BR); Maria Marta Moreira Crelier, Rio de Janeiro (BR); Bruno Charles Do Couto, Rio de Janeiro (BR); Thiago Andrade Delfino Da Silva, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 306 days.

(21) Appl. No.: 17/986,580

(22) Filed: Nov. 14, 2022

(65) Prior Publication Data
US 2023/0152295 A1 May 18, 2023

(30) Foreign Application Priority Data
Nov. 12, 2021 (BR) .................. 10 2021 022892 0

(51) Int. Cl.
*G01N 33/28* (2006.01)

(52) U.S. Cl.
CPC ............................. *G01N 33/2847* (2013.01)

(58) Field of Classification Search
CPC .................................................. G01N 33/2847
See application file for complete search history.

(56) References Cited

U.S. PATENT DOCUMENTS

2016/0317947 A1* 11/2016 Sanchez ................. C10G 21/06
2021/0396731 A1* 12/2021 Ahmed .................... G01N 1/18

OTHER PUBLICATIONS

Almeida, Careli F. (2017) "Planejamento De Experimentos Para análise Da Influência Do Teor De Água Na Incerteza De Medição De Vazão De Óleo Com Medidores Ultrassônicos", Pontifical Catholic University of Rio de Janeiro, 109 pages.

(Continued)

*Primary Examiner* — Kristina M Deherrera
*Assistant Examiner* — Jean F Morello
(74) *Attorney, Agent, or Firm* — Morrison & Foerster LLP (57) ABSTRACT

The present invention addresses to a method for characterizing water produced in oil samples containing water with contents below 0.5%, by measuring the analytes of interest directly in the oil containing the emulsified water. For this, it is necessary to carry out filtrations to remove possible suspended solids, since they may interfere with the composition of the water. The method proposed in the present invention provides methodologies with and without interference in the equilibrium by washing the oil with distilled water, measuring the analytes of interest directly in the oil.

6 Claims, 8 Drawing Sheets

(56) References Cited

OTHER PUBLICATIONS

Endres et al. (2020) "Risk Assessment and Management of Mineral Scale in a Production Well with Selective Completion—Case Study in Santos Basin Pre-Salt", Rio Oil & Gas Expo And Conference, ISSN 2525-7579, 12 pages.

Frinhani et al. (2007) "Estudo Da Correlação Do Teor De Sal E Bsw Em Petróleos Do Estado Do Espírito Santo", 30a Reunião Anual da Sociedade Brasileira de Química, 1 page.

* cited by examiner

METHOD FOR DETERMINING THE COMPOSITION OF WATER IN LOW BSW OILS

CROSS-REFERENCE TO RELATED APPLICATION

This application claims priority to Brazilian Application No. 10 2021 022892 0, filed on Nov. 12, 2021, and entitled "METHOD FOR DETERMINING THE COMPOSITION OF WATER IN LOW BSW OILS," the disclosure of which is incorporated herein by reference in its entirety.

FIELD OF THE INVENTION

The present invention addresses to a method for determining the composition of water in oils with basic sediment and water, hereinafter ("BSW"), below 0.5% (water content), with application in the field of Oil Production Processes, aiming at reducing losses by formation of premature scaling in oil production units.

DESCRIPTION OF THE STATE OF THE ART

Currently, there are no data on the chemical composition of the present water in oils with BSW below 0.5%. This is because the use of separation processes, such as centrifugation with benchtop equipment, does not allow the separation of water from oil efficiently in this proportion, that is, until now, it has not been possible to characterize water considering matrices with low water concentration. This fact implies a lack of predictability of possible scaling problems throughout the production of the wells and makes studies and predictions related to scaling and rock fluid interaction (RFI) unfeasible.

One of the options is to evaluate whether the analysis of the elements of interest directly in the oil could be attributed to the present water, without causing gross errors. Currently, the methodologies used to obtain inorganic compounds (ICP-OES), water content (Karl Fischer titration) and total chlorine (MWDFRX) work very well for an oily matrix, and are available for use.

However, it is not prudent to attribute the contents of the compounds measured by these methodologies directly to the water because the suspended material existing in the analyzed oil will be erroneously attributed to the composition of the water. So, the challenge is to establish a methodology that guarantees that such suspended materials are removed prior to the analyses. For this, it is necessary to establish the best oil filtration condition to ensure the removal of suspended material.

Another possibility is to evaluate aqueous phase separation techniques with interference in the equilibrium, after establishing the best way to filter the oil. The idea is to increase the oil with known amounts of distilled water, in proportions separable by the traditional centrifugation process, and then evaluate the contents of the compounds of interest in this new water. The final composition of the water is obtained by performing the dilution calculations. The difficulty lies in obtaining a low dilution that allows separation and does not generate high errors or compromise quantification due to the dilution effect. It is important to point out that, even in this approach, it is necessary to consider the preliminary oil filtration due to the possibility of interaction of the water added to the system and partial solubilization of the solids. Given the adverse effect caused by dilution, this issue cannot be ignored.

The existing approaches in the literature always apply centrifugation to isolate the water and then perform the analyses to measure the analytes of interest in this obtained water. However, conventional centrifuges existing in laboratories, even at very high rotations and temperatures, cannot efficiently separate waters from oils, with water contents below 0.5%, making the analysis of these waters unfeasible and, therefore, making it impossible to predict problems related to scaling or to rock-fluid interaction effects. This causes a series of problems, among which the greatest impact is the loss of premature production, which means large financial losses.

Another need is related to alkalinity measurements. Currently, the analysis of alkalinity in oils with a BSW lower than 0.5% is not feasible, because it is not possible to obtain integrated water to carry out the titration.

Additionally, due to the difficulty of obtaining integrated water in the BSW scenario of less than 0.5%, the analysis of chemical tracers (such as halobenzoics) is also compromised, since the analysis traditionally used is based on the extraction of acids from water using solid phase extraction (SPE) cartridges and performing their quantification by mass spectrometry.

So, the challenge is to establish a methodology that guarantees that such suspended materials are removed prior to analysis.

In the study by ENDRES, L.; PERRELLI, D. C.; ARAUJO, B. C. S. (2020) "Risk evaluation and management of mineral scale in a production well with selective completion-case study in Santos Basin pre-salt", *Rio Oil & Gas Expo and Conference*, ISSN 2525-7579, there is evaluated the risk of saline precipitation from the chemical composition of the water produced individually in each producing interval of a well selectively completed in two intervals/zones, compared to the usual production condition, with the two well intervals open.

In the reference by FRINHANI, R. Q. et al. (2007) "Estudo da correlação do teor de sal e BSW em petróleos do estado do Espírito Santo" ("Study of the correlation of salt content and BSW in oils from the state of Espírito Santo"), $30^{th}$ *Annual Meeting of the Brazilian Chemical Society*, there is reported the importance of monitoring in face of BSW determinations of oil samples with unknown profiles in order to do verify, so, the presence of dissolved salts from the formation water and provide mitigating actions to reduce BSW levels to acceptable levels, avoiding damage to the refining process.

The study by ALMEIDA, F. C. (2017) "Planejamento de experimentos para análise da influência do teor de água na incerteza de medição de vazão de óleo com medidores ultrassônicos" ("Planning of experiments to analyze the influence of water content on the uncertainty of oil flow rate measurement with ultrasonic meters"), 109f., Dissertation (Master's)—Pontifical Catholic University of Rio de Janeiro, Postgraduate Program in Metrology for Quality and Innovation, evaluates the influence of water content and meter factor on the uncertainty of oil metering grids using ultrasonic meters.

In view of this, no document of the state of the art discloses a method for obtaining the composition of the water produced in very low proportions in its oils (below 0.5%), simply overcoming the non-separation of phases by centrifugation such as that of the present invention.

In this way, in order to solve such problems, the present invention was developed, by means of a method of obtaining data regarding the integrated water by measurement directly in the oil without and with interference in the equilibrium (by addition/washing with distilled water), and further reports the activities related to alkalinity measurements and the possibility of measuring tracers (such as halo-benzoic acids) in the scenario of oil with BSW below 0.5%.

The present invention presents advantages of reducing losses due to premature scale formation in units that have oil production in these BSW conditions, with the water composition data, an early evaluation of these scales and also an evaluation of rock fluid interactions in the reservoir are possible.

BRIEF DESCRIPTION OF THE INVENTION

The present invention addresses to a method for determining the composition of water in oils with BSW below 0.5%, by measuring the analytes of interest directly in the oil containing the emulsified water, performing filtrations to remove possible solids in suspension, since they can interfere with the composition of the water. The proposed method provides a method with and without interference in the equilibrium by washing the oil with distilled water and measuring the analytes of interest directly in the oil.

The method of the present invention is applied to the analysis of water composition in oil exploration and production.

BRIEF DESCRIPTION OF DRAWINGS

The present invention will be described in more detail below, with reference to the attached figures which, in a schematic form and not limiting the inventive scope, represent examples of its embodiment. In the drawings, there are.

DETAILED DESCRIPTION OF THE INVENTION

Figure 1:
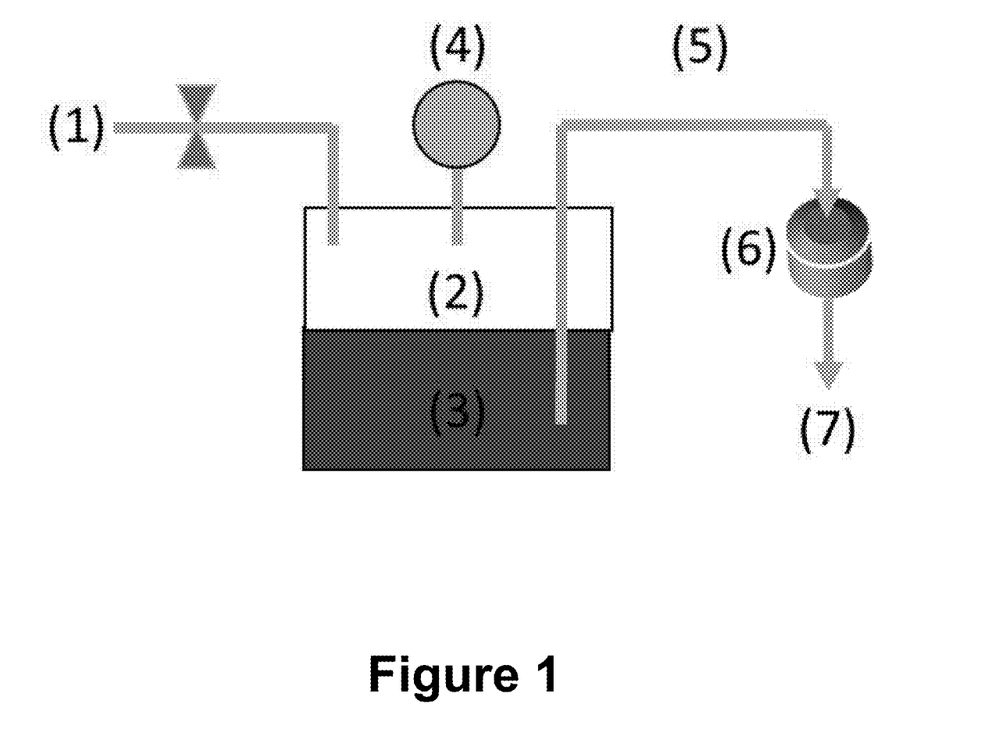
FIG. 1 illustrating a system for pumping $N_2$ under pressure, where there are represented: (1) $N_2$; (2) $N_2$ pressure vessel; (3) oil pressure vessel; (4) manometer; (5) oil transfer line; (6) filter; and (7) filtered oil.

The method of the present invention comprises subjecting the oil samples to filtration, using a membrane support system being carried out by pumping (using, for example, peristaltic pumps) or positive pressure (for example, with a pressurized pan with $N_2$), under heating (40 to 60° C.), as illustrated in FIG. 1. The membranes used are nylon membranes, with pore diameters of 0.45 μm, 1.2 μm, 5 μm and 11 μm.

The determinations of water content in oil were made by volumetric titration (volumetric Karl Fischer).

The determination of metals Mg, Na, K, Ca, Sr, Ba, Fe, Zn in oil, unfiltered and filtered, was performed by determination of Metals and Silicon by Atomic Absorption Techniques (AAS) and atomic absorption spectrometry with inductively coupled optical emission plasma (ICP-AES), whose samples are incinerated and the ashes obtained are mineralized. The solution obtained is analyzed by the techniques of AAS or ICP-AES to obtain the contents of the elements. To determine Si and Al, the ashes are melted using a specific flux mixture The determination of total chlorine content was performed directly in the oil according to ASTM D7536 guidelines, using monochromatic wavelength dispersion X-ray fluorescence spectroscopy (MWDFRX). In short, a monochromatic beam with a wavelength tuned to excite the chlorine electrons in a sample. The fluorescent radiation emitted by the chlorine is measured. The measurement intensity is converted into concentration through a calibration curve.

More specifically, the method for determining the composition of water in oils with BSW below 0.5% according to the present invention comprises the following steps:

(a) Homogenizing the oil samples as received for at least 30 minutes;

(b) Filtering the oil samples using a system for pumping under pressure using a peristaltic pump and a pressure pan with $N_2$, under heating (40 to 60° C.). The used nylon membranes have a pore diameter of 0.45 μm, 1.2 μm, 5 μm or 11 μm, preferably 11 μm;

(c) Determining the water content in the oil samples by titration (volumetric Karl Fischer);

(d) Determining the metals in the oil samples by means of incineration, in which the ashes obtained are mineralized. The solution obtained is analyzed using AAS or ICP-AES techniques. If there is a need to determine Si and Al, the ashes are melted using a specific flux mixture. For the determination of metals in integrated water, the aqueous sample is filtered, diluted minimally 10 to 20 times, and then this solution is analyzed by ICP-OES. The concentration range to be determined in the final solution that will be injected into the equipment is from 0.1 to 10 mg/Kg;

(e) Determining the total chlorine content directly in oil samples using monochromatic wavelength scattering X-ray fluorescence spectroscopy (MWDFRX), where a monochromatic beam with a wavelength is set to excite chlorine electrons in a sample. The fluorescent radiation emitted by the chlorine is measured. The intensity of the measurements is converted into concentration through a calibration curve, the minimum limit being 1 mg/Kg;

(f) Performing liquid-liquid extraction with 100 grams of oil sample by adding 5 grams/mL or other proportion of interest of distilled water. The mixture is homogenized for 2 hours. After this period, a demulsifier is added, and a new homogenization is carried out for another 5 minutes. Or, a demulsifier is added before the homogenization. The centrifuge tube containing the homogenized mixture is centrifuged for 30 minutes. Once this is done, the oil with the separated water is poured into a separating funnel to obtain the water;

(g) The determination of the chloride content directly in integrated water or in the aqueous extract is carried out by potentiometric titration, in which the sample is titrated with silver nitrate using a glass electrode containing a silver electrode. The end point of the titration occurs when there is an intense change in voltage when small and constant amounts of silver nitrate are added;

(h) The determination of the alkalinity directly in the aqueous extract is carried out by titration with acidic solution, results expressed in meq/L;

(i) Performing the liquid-liquid extraction for tracer evaluation through a volume of 500 mL of oil adding 175 mL of toluene, 50 mL of saline solution (35 g/100 mL of NaCl) and 10 drops of demulsifier. The mixture must be homogenized in a mechanical stirrer for 30 minutes and then subjected to centrifugation for two hours at 40° C. under rotation of 11000 rpm. Carry out three successive washes. At the end, water is obtained from the washing of 5 liters of oil. The pH of this water is adjusted with potassium hydroxide to pH 8;

(j) Performing the analysis of tracers, such as halobenzoics in the aqueous phase obtained in step "(i)" using extraction by SPE acidification and derivatization to qualify the presence by gas chromatography coupled to high resolution mass spectrometry (GC/HR-MS) or gas chromatography coupled to triple quadrupole mass spectrometry;

EXAMPLES

The following examples are presented in order to more fully illustrate the nature of the present invention and the manner of practicing the same, without, however, being considered as limiting its content.

In summary, the oil homogenization protocol was applied, filtration in nylon membrane with pores between 0.45 and 11 mm, in a sample with BSW greater than 0.5%. The filtered fluid was analyzed to obtain the content of water, metals and chloride, the obtained contents were attributed to the water whose content was measured by Karl Fischer, and, in addition, integrated water was obtained by centrifugation, analyzed to obtain of the same compounds analyzed directly in the oil. The compositional results obtained were compared and their equivalence proved. In addition, the proportion of chloride and sodium compounds was monitored before and after application of the protocol. The measurement of chlorine and sodium must be equal, as they are in high proportion, they must not be affected above the measurement error. It was replicated for samples with BSW below 0.5% to evaluate the results.

Example 1: Filtration with 0.45 μm Membrane at 60° C.

The filtration was tested with the pumping system pressurized with $N_2$ at a temperature close to 60° C. using the 0.45-micron nylon filter. Filtration was carried out, but with difficulties. Little oil volume was obtained due to clogs. They probably occurred due to the precipitation of paraffins in the lines and in the filter. Even though the entire system is covered by heating tapes, some region probably did not get warm enough. However, performing repeated filtrations, sufficient quantities were obtained to perform the analyses.

Even with the pumping system working, due to the fact that it is quite laborious to carry out the filtrations by this system and because it is entirely inserted in the oven together with the oil sample, making interventions difficult, filtrations were evaluated with a system using a peristaltic pump of positive pressure that forces the fluid to pass through the filtration membrane. Due to the good results, most of the filtrations were performed in this system.

Example 2: Contents of Water, Metals and Direct Chlorine in Unfiltered and Filtered Oils The results of the evaluation of the water content were obtained before and after filtration in a nylon fiber filter with pores of 0.45 μm under temperatures close to 60° C. are presented comparatively in Table 1.

TABLE 1

Results of water content obtained by Karl Fischer in oils before and after filtration through 0.45 μm nylon fiber membrane.

| SCAD | Water content in unfiltered oil (% m/m) | Water content in the filtered oil (% m/m) | Remaining proportion in relation to the original water content % |
| --- | --- | --- | --- |
| 2017-003561-17 | 800 (mg/Kg) | 448 (mg/Kg) | 56.0 |
| 2017-011077-06 | 0.39 | 0.16 | 41.0 |
| 2017-016088-29 | 0.9 | 0.19 | 21.1 |
| 2017-016954-54 | 0.75 | 0.58 | 77.3 |
| 2017-017339-92 | 0.39 | 0.21 | 53.8 |
| 2017-017340-26 | 0.32 | 0.27 | 84.4 |
| 2017-017341-07 | 0.29 | 0.2 | 69.0 |
| 2018-000939-75 | 769 (mg/Kg) | 416 (mg/Kg) | 54.1 |

Table 1 shows that there were considerable reductions in the amount of water in the samples. The reduction in water content is an indication that its composition may have been compromised.

Regardless, the results of the compounds of interest were obtained directly in some oils before and after filtration, the compounds Mg, Na, K, Ca, Sr, Ba, Fe, Al and Si by ICP-AES and chlorine total by MWDFRX. The obtained results are reported in Table 2.

TABLE 2

Results of measurements of the compounds of interest directly in unfiltered
(S) and filtered (F) oils in 0.45 μm membrane at 60° C.

| SAMPLES | | Mg | Na | K | Ca | Sr | Ba | Fe $mg \cdot Kg^{-1}$ | Zn | Al | Si | Chlorine |
|---|---|---|---|---|---|---|---|---|---|---|---|---|
| 2017-003561-17 | S | <0.5 | 8.0 | <1 | 5.0 | <0.5 | <0.5 | <0.5 | <0.5 | — | — | 75 |
| | F | <0.5 | 10 | 4.5 | 2.8 | <0.5 | <0.5 | <0.5 | <0.5 | 1.0 | <1.0 | 48.4 |
| 2017-011077-06 | S | 7.4 | 280 | 11 | 41 | 3.9 | <0.5 | <0.5 | <0.5 | 1.1 | <1 | 554 |
| | F | <0.5 | 1 | <1.0 | 1.7 | <0.5 | <0.5 | <0.5 | <0.5 | — | — | 40.8 |
| 2017-016088-29 | S | 0.8 | 150 | 11 | 4 | 0.7 | <0.5 | 1.4--3.8 | <0.5 | 2.2 | 3.1 | 321 |
| | F | 1 | 19 | 1 | 1 | <0.5 | <0.5 | <0.5 | <0.5 | <1 | <1 | 83 |
| 2017-016954-54 | S | 17 | 590 | 24 | 89 | 200 | <0.5 | 1.4 | <0.5 | <0.1 | <0.1 | 973 |
| | F | 0.5 | 64 | 3.7 | 0.9 | <0.5 | <0.5 | 2.6 | <0.5 | — | — | 973 |
| 2017-017339-92 | S | 9.5 | 350 | 14 | 57 | 4.9 | <0.5 | 2 | <0.5 | <1 | 1.7 | 591 |
| | F | 7.2 | 290 | 12 | 41 | 99 | <0.5 | <0.5 | <0.5 | <1 | <1 | 566 |
| 2017-017340-26 | S | 8.6 | 290 | 14 | 43 | 4.3 | <0.5 | <0.5 | 1.5 | <1 | 1.6-4.4 | 541 |
| | F | 8.4 | 220 | 11 | 48 | 4.3 | <0.5 | 0.83/<0.5 | <0.5 | <1 | <1 | 482 |
| 2017-017341-07 | S | 1 | 120 | 7.4 | 3.5 | <0.5 | <0.5 | <0.5 | <0.5 | <1 | 2.4-7.2 | 183 |
| | F | 12 | 510 | 19 | 72 | 5.9 | <0.5 | 1.2 | <0.5 | <1 | <1 | 229 |
| 2018-000939-75 | S | <0.5 | 7.6 | <1.0 | 11 | 1.9 | 0.5 | <0.5 | <0.5 | <1 | <1 | 61.9 |
| | F | <0.5 | 7.2 | <1 | 8.9 | 1.5 | <0.5 | <0.5 | <0.5 | <1 | <1 | 51.3 |

It can be seen from the results of chlorine and sodium in Table 2 that there are very high differences between their unfiltered and filtered contents. Anyway, to evaluate whether these differences are really important, the results of the water content (Table 1) were used to calculate the contents of the elements of interest in the water from the contents reported in Table 2. From this, the total contents of chlorine obtained by the MWDFRX technique and calculated for water were considered as chloride, since chlorine values other than in the form of chloride are not expected to be higher than the errors built into the account when considering the significant numbers or even the measurement errors.

The thorough examination whether or not there was a compositional change remains related to obtaining a minimal change in chlorine and sodium concentrations. These compounds are normally in high concentrations in water, so their calculated concentrations must be close to each other. This minimum value does not yet exist, so it was decided to analyze as many samples as possible that were available in the laboratory. The obtained contents are reported in Table 3; to facilitate visualization, they were not reported in scientific notation with 2 significant figures.

Figure 2:
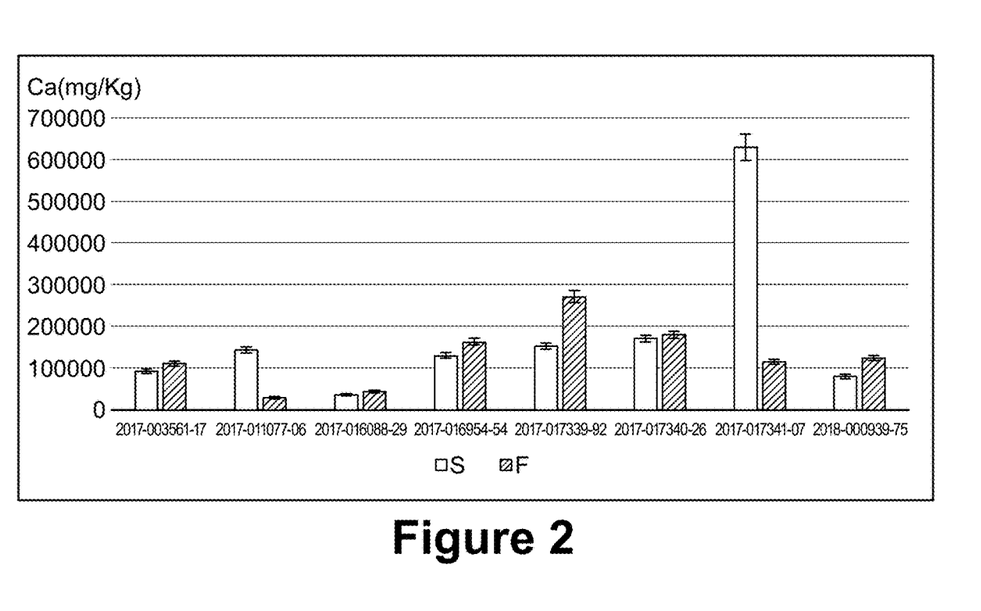
FIG. 2 illustrating a graph of sodium content attributed to water from measurements in unfiltered oil and filtered at 60° C.
Figure 3:
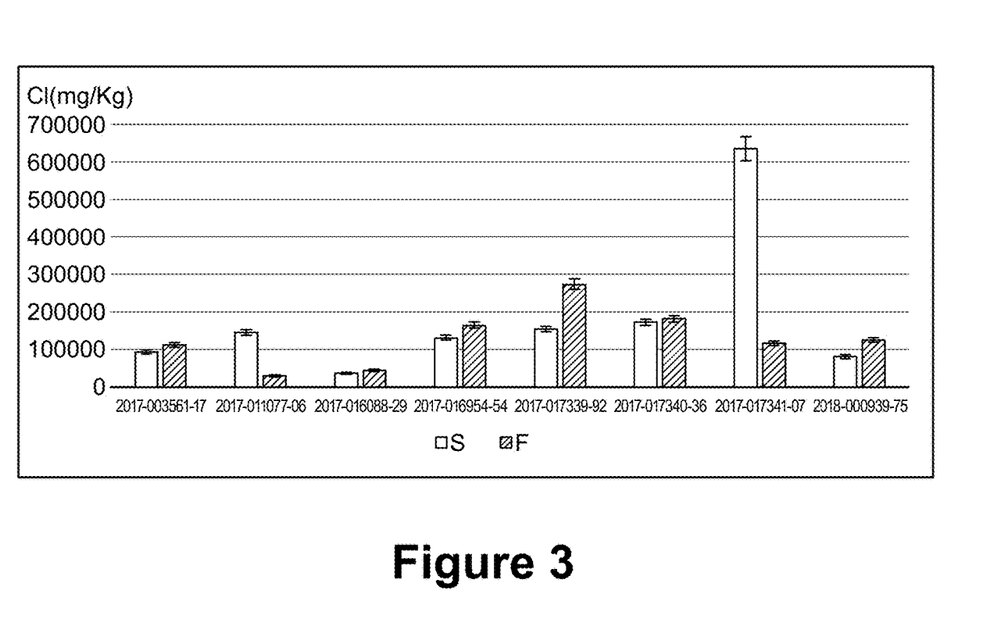
FIG. 3 illustrating a graph of chlorine content attributed to water from measurements in unfiltered oil and filtered at 60° C.

To comparatively evaluate the results presented in Table 3, the graphs of FIGS. 2 and 3 were obtained, which respectively are the sodium and chlorine contents with their respective measurement errors, the estimated value for chloride is 5% and for sodium will be considered 10% (Table 2).

When comparing the unfiltered and filtered results of FIG. 2, it is observed that only the oil sample "2017-017-340-26" has the same results. The contents of the oil samples "2017-011077-06" and "2017-017341-07" showed extremely discrepant results. The oil samples "2017-016-088-29", "2017-017339-92", "2017-017340-26" and "2018-000939-75" showed results of sodium content closer to each other, but they are different by the error criterion. When evaluating the chlorine levels in FIG. 3, there is also a huge discrepancy in the results of the samples "2017-011077-06" and "2017-017-340-26". And once again, only the sample "2017-017-340-26" showed equality between the results considering the error. These results demonstrate that these samples suffered great interference, at least greater than the error of the measurement used in the composition of the water, which makes it impossible to use the other results in the evaluation of the influence of filtration.

TABLE 3

Results of the calculation of the compounds of interest attributed to the water from the
measurements in the unfiltered (S) and filtered (F) oils in 0.45 μm membrane at 60° C.

| SAMPLES | | Mg | Na | K | Ca | Sr | Ba | Fe $mg \cdot Kg^{-1}$ | Zn | Al | Si | Chlorine |
|---|---|---|---|---|---|---|---|---|---|---|---|---|
| 2017-003561-17 | S | — | 9800 | — | 6100 | — | — | — | — | — | — | 92000 |
| | F | — | 22000 | 10000 | 6200 | — | — | — | — | 2200 | — | 110000 |
| 2017-011077-06 | S | 1900 | 71800 | 2800 | 10000 | 1000 | — | — | — | 280 | — | 142000 |
| | F | — | 710 | — | 1200 | — | — | — | — | — | — | 29100 |
| 2017-016088-29 | S | 90 | 16700 | 1200 | 400 | 78 | — | 170-420 | — | 240 | 340 | 35700 |
| | F | 130 | 26500 | 1200 | 12 | 9 | — | — | — | — | 26 | 43000 |
| 2017-016954-54 | S | 2300 | 78700 | 3200 | 12000 | 26700 | — | 190 | — | — | — | 130000 |
| | F | 86 | 11000 | 640 | 150 | — | — | 450 | — | — | — | 162000 |
| 2017-017339-92 | S | 2400 | 90000 | 3600 | 15000 | 1200 | — | 500 | — | — | 440 | 152000 |
| | F | 3400 | 138000 | 5700 | 20000 | 4700 | — | — | — | — | — | 270000 |
| 2017-017340-26 | S | 2700 | 91000 | 4400 | 13000 | 1300 | — | — | 470 | — | 500-1400 | 170000 |
| | F | 3100 | 81000 | 4100 | 18000 | 1600 | — | 260/<160 | — | — | — | 179000 |
| 2017-017341-07 | S | 340 | 41400 | 2600 | 1200 | — | — | — | — | — | 830-2500 | 631000 |
| | F | 6000 | 255000 | 9500 | 36000 | 3000 | — | 600 | — | — | — | 114000 |
| 2018-000939-75 | S | — | 9900 | — | 14000 | 2500 | 650 | — | — | 1300 | 1300 | 81000 |
| | F | — | 17000 | — | 21000 | 3600 | — | — | — | — | — | 123000 |

Another way of evaluating was performed by obtaining the integrated water from the sample "2017-016954-54". This was done by centrifugation and its composition was obtained from ICP-OES. The comparison of these results with the results obtained by direct measurement in integrated water, direct measurement in unfiltered and filtered oil is presented in Table 4. The comparison of sodium and chloride is reported in FIG. 4.

Figure 5:
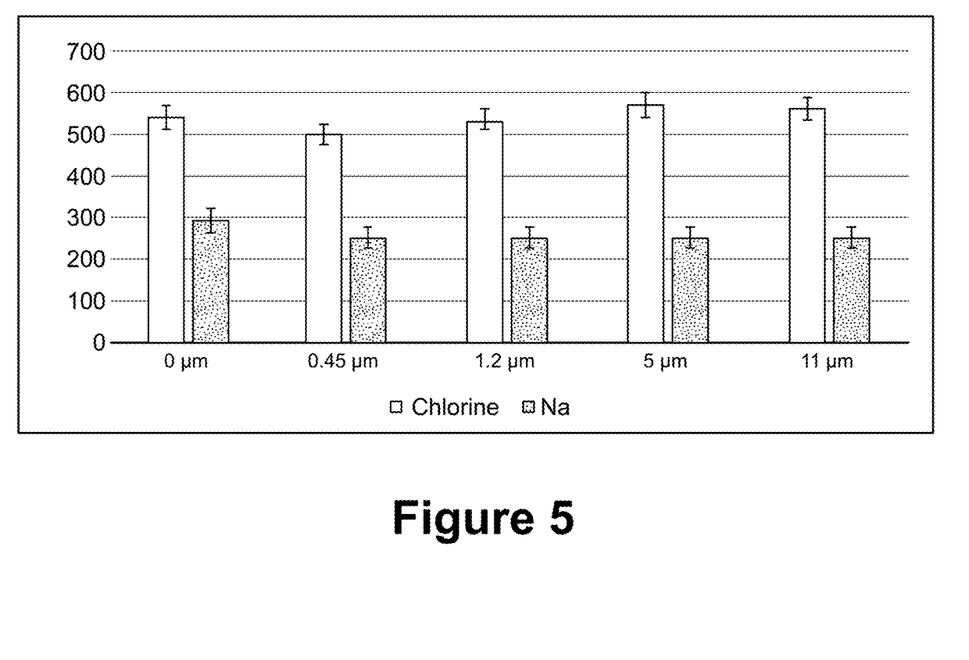
FIG. 5 illustrating a graph of the comparative evaluation of the chlorine and sodium contents of the oil sample "2017-017340-26" without filtering (S) and filtered (F) with membranes of pore diameters 0.45, 1.1, 5 and 11 μm at 40° C.

It is observed, when evaluating the results of Table 5 and FIG. 5, that they are adherent to each other. This result indicates that the filtration did not disturb the system so much as to make filtration with different membrane pore diameters unfeasible. Accordingly, the water composition was attributed, obtaining the results of Table 6 and comparison of sodium and chloride in FIG. 6.

TABLE 4

Comparative results of the composition of integrated water and measurements directly in the oil "2017-016954-54", unfiltered (S) and filtered (F) at 60° C.

| SAMPLE | | Mg | Na | K | Ca | Sr mg · Kg$^{-1}$ | Ba | Fe | Zn | Al | Si | Cl— |
|---|---|---|---|---|---|---|---|---|---|---|---|---|
| 2017-016954-54 | Oil (S) | 2300 | 78700 | 3200 | 12000 | 26700 | — | 190 | — | — | — | 130000 |
| | Oil (F) | 86 | 11000 | 640 | 150 | — | — | 450 | — | — | — | 162000 |
| | Water (mg · L$^{-1}$) | 2400 | 71800 | 3200 | 11000 | 1200 | 3.1 | — | — | — | 9 | 140000 |
| | Water (mg · Kg$^{-1}$) | 2800 | 84700 | 3800 | 13000 | 1400 | 3.7 | — | — | — | 11 | 170000 |

(*) density = 1.18, estimated

Figure 4:
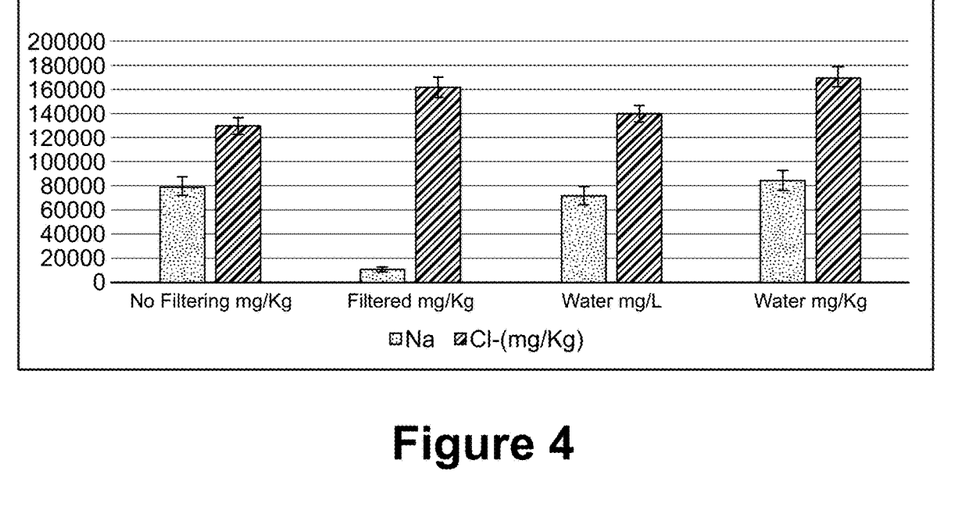
FIG. 4 illustrating a graph with comparative results of sodium and chloride contents by direct measurement in water and attributed to water by measurements in oil "2017-003561-17" at 60° C.

It is observed from the evaluation of Table 4 and the graph of FIG. 4 that the results indicate that filtration is interfering with the composition of the water. The sodium content in the filtrate was much lower than the actual content measured in water and the chloride content was closer, but still higher than that measured directly in the water. Therefore, the filtration procedure must be adjusted to obtain a coherent methodology. The idea found was to reduce the filtration temperature, and also to evaluate membranes with pore diameters greater than 0.45 μm, used until now. The results will be discussed in the next topic.

Example 3: Filtration with 0.45, 1.2, 5 and 11 μm Nylon Membrane at 40° C.

To evaluate the effect of the pore diameter, new filtrations were performed using the diameters 0.45, 1.2, 5 and 11 μm at 40° C. The procedure was performed on the oil sample "2017-017340-26" and on the sample SCAD "2017-016954-54", the latter with BSW above 0.5%, for comparative purposes; as explained above, this would be the only way to obtain integrated water for characterization.

The filtered oils were again sent for evaluation of the content of water, chlorine and the elements magnesium, sodium, potassium, calcium and strontium. The results obtained with the sample "2017-017340-26" are reported in Tables 5 and 6. The iron, zinc, aluminum and silicon compounds presented contents below 1 mg·Kg$^{-1}$; therefore, they will not be reported in the tables. To evaluate whether there were differences in the measurements, the comparative graph in FIG. 4 was obtained with the sodium and chlorine contents.

TABLE 5

Results of content of water, Cl, Na, Mg, K, Ca and Sr of sample "2017-017340-26, without filtering and filtered with membranes with pore diameters of 0.45, 1.2, 5 and 11 μm at 40° C.

| Filtration | Water content by Karl Fischer (%) | Contents in oil mg · Kg$^{-1}$ | | | | | |
| --- | --- | --- | --- | --- | --- | --- | --- |
| | | Chlorine | Mg | Na | K | Ca | Sr |
| Without filtering | 0.32 | 541 | 8.6 | 290 | 14 | 43 | 4.3 |
| F 0.45 μm @40° C. | 0.24 | 500 | 8.3 | 250 | 12 | 42 | 4.4 |
| F 1.2 μm @40° C. | 0.30 | 534 | 8.3 | 250 | 12 | 42 | 4.5 |
| F 5.0 μm @40° C. | 0.27 | 572 | 8.0 | 250 | 12 | 44 | 5.0 |
| F 11 μm @40° C. | 0.29 | 561 | 8.2 | 250 | 12 | 39 | 4.3 |

TABLE 6

Results of Cl, Na, Mg, K, Ca and Sr attributed to the water of the sample "2017-017340-26" without filtering and filtered with membranes of diameters 0.45, 1.2, 5 and 11 μm at 40° C.

| SAMPLES | Calculated contents in water (mg/Kg) | | | | | |
| --- | --- | --- | --- | --- | --- | --- |
| | Chloride | Mg | Na | K | Ca | Sr |
| No filtering | 169000 | 2700 | 90600 | 4400 | 1300 | 1300 |
| F 0.45 μm | 208000 | 3100 | 104000 | 5000 | 1800 | 1800 |
| F 1.2 μm | 198000 | 3100 | 92600 | 4400 | 1600 | 1700 |
| F 5.0 μm | 197000 | 2900 | 86200 | 4100 | 1500 | 1600 |
| F 11 μm | 187000 | 2700 | 83300 | 4000 | 1300 | 1400 |

Figure 6:
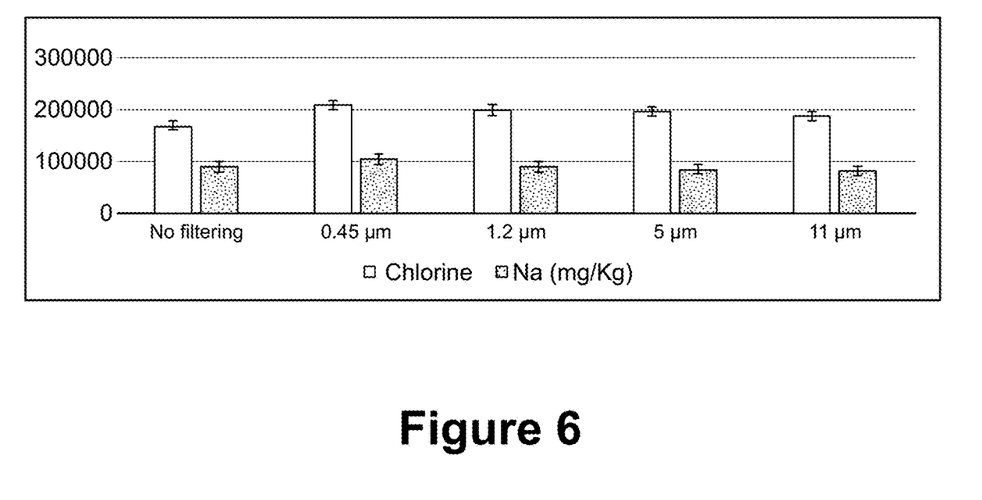
FIG. 6 illustrating a graph of the comparative evaluation of the chlorine and sodium contents of the sample "2017-017340-26" without filtering and filtered (F) with membranes with pore diameters of 0.45, 1.2, 5 and 11 μm at 40° C.

It can be seen from Table 6 and FIG. 6 that the sodium results are converging with each other, indicating that the perturbations were not significant. As for the chloride results, it is observed that the unfiltered sample has a different result from the others; for the other samples, this did not occur (they are similar to each other). Issues associated with sampling may have interfered with the data obtained, considering that they are different measurement techniques.

The results of the measurements of the compounds of interest with the sample "2017-016954-54" are reported in Table 7. To evaluate whether there were differences in the measurements, the graph in FIG. 7 was obtained comparing the results of sodium and chlorine.

TABLE 7

Results of the water content, Cl, Na, Mg, K, Ca and Sr of the sample "2017-016954-54" without filtering and filtered with membranes of diameters 1.2, 5 and 11 μm at 40° C.

| Filtration | Water content by Karl Fischer (%) | Contents in oil mg/Kg | | | | | | |
|---|---|---|---|---|---|---|---|---|
| | | Chlorine | Mg | Na | K | Ca | Sr | Fe |
| No filtering | 0.75 | 973 | 17 | 590 | 24 | 89 | 200 | 1.4 |
| F 1.2 μm | 0.53 | 950 | 12 | 480 | 27 | 81 | 4 | <0.5 |
| F 5.0 μm | 0.55 | 1073 | 12 | 450 | 26 | 76 | 3.7 | <0.5 |
| F 11 μm | 0.63 | 1051 | 17 | 495 | 22 | 88 | 9 | <0.5 |

Figure 7:
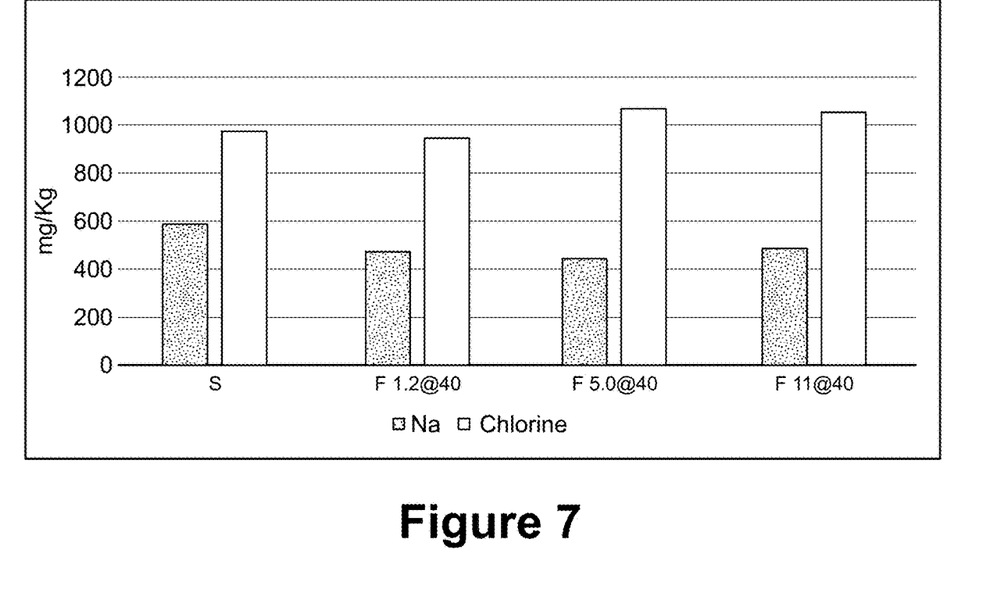
FIG. 7 illustrating a graph of the comparative evaluation of the chlorine and sodium contents of the sample "2017-017340-26 without filtering (S) and filtered (F) with membranes of diameters 1.2, 5 and 11 μm at 40° C.

By the results of Table 7 and by the comparison of FIG. 7, it is observed that the sodium content of the sample without filtering presented a result above the filtrations 1, 2, 5 and 11 μm. These three filtrations showed convergent results among themselves. The result suggests that for this proportion of water there are still slight disturbances in the filtrations.

Figure 8:
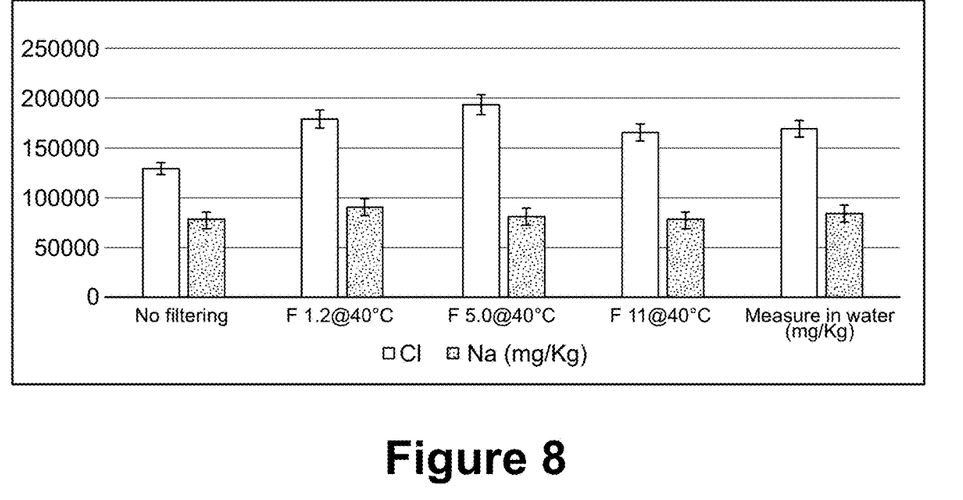
FIG. 8 illustrating a graph of the comparative evaluation of the chlorine and sodium contents of the sample "2017-017340-26" measured in water and oil attributed to unfiltered and filtered water (F) with membranes of diameters 1.2, 5 and 11 μm.

Accordingly, the compounds of interest were attributed to the water composition as shown in Table 7 and FIG. 8.

The results for sodium and chloride reported in Table 8 and FIG. 8, including integrated water, are converging. In general, the results were quite similar to each other, with some differences that are acceptable considering the proposed approach.

TABLE 8

Results of Cl, Na, Mg, K, Ca and Sr measured and attributed to the water of the sample "2017-016954-54" without filtering and filtered (F) with membranes of diameters 1, 2, 5 and 11 μm at 40° C.

| Samples | Calculated contents in water (mg/Kg) | | | | | | | | |
|---|---|---|---|---|---|---|---|---|---|
| | Cl | Mg | Na | K | Ca | Sr | Ba | Fe | Si |
| Without filtering | 130000 | 2300 | 79000 | 3200 | 12000 | 27000 | <67 | 190 | <130 |
| F 1.2 μm | 180000 | 2300 | 90600 | 5100 | 15000 | 800 | <94 | <94 | 230 |
| F 5.0 μm | 195000 | 2200 | 81800 | 4700 | 14000 | 670 | <91 | <91 | <180 |
| F 11 μm | 167000 | 2700 | 78600 | 3500 | 14000 | 1400 | <79 | <79 | <160 |
| Measured in water (mg/L) | 140000 | 2400 | 71800 | 3200 | 11000 | 1200 | 3.1 | — | 9 |
| Measured in water (mg/Kg)* | 170000 | 2800 | 84700 | 3800 | 13000 | 1400 | 3.7 | — | 11 |

Considering that the variable that most influences the change in composition seems to be the temperature and not the pore diameter of the membrane used in the filtration, the use of the membrane with a diameter of 11 μm was defined in the filtration at a temperature of 40° C. This decision is based on the greater ease of obtaining filtrate, both in terms of filtration time and volume. In this way, there is less possibility of influence of the procedure on the precipitation of soluble salts present in water, in case of working in matrices different from the one used in this work.

Example 3: Application of the Methodology to Other Samples Available in the Laboratory From the moment the results of Example 2 were obtained, it was decided to apply the methodology to the other samples available in the laboratory, listed in Table 9. The water contents obtained by Karl Fischer without filtering and filtered with 11 μm membrane are also reported in the table.

TABLE 9

Karl Fischer water content results in unfiltered and filtered oil samples.

| SCAD | Karl Fischer without filtering | Karl Fischer Filtered 11 μm | Proportion of content in relation to the original water content % |
|---|---|---|---|
| 2017-011077-06 | 0.39% | 0.36% | 92 |
| 2017-011650-64 | 305 mg/Kg | 222 mg/Kg | 73 |
| 2017-017339-92 | 0.39% | 0.32% | 82 |
| 2017-017341-07 | 0.29% | 0.23% | 79 |
| 2018-000938-94 | 0.39% | 0.35% | 90 |
| 2018-007393-10 | 781 mg/Kg | 603 mg/Kg | 77 |
| 2018-012019-09 | 0.12% | 787 mg/Kg | 66 |
| 2018-012020-42 | 0.12% | 871 mg/Kg | 73 |
| 2019-029859-64 | 299 mg/Kg | 266 mg/Kg | 89 |

It can be seen from Table 9 that there were further reductions in the amount of water in the samples after filtration, but to a lesser extent, when compared to the changes in filtrations at 60° C. with a 0.45-micron membrane. It is believed that this smaller reduction is already an indication that the results of the water composition probably do not change to the point of invalidating the measure.

Thus, the quantification of the compounds of interest was obtained directly in some oils before and after filtration with a membrane of 11 μm. The results found are reported in Table 10.

It is observed in Table 10 that only the results of the oil samples "2017-011650-64" and "2019-029859-64" showed very different sodium contents between the filtered and unfiltered samples. For chloride, there is no result that can be highlighted. The contents found were attributed to the water using the water contents reported in Table 9. Considering the water content in the sample, it is possible to recalculate the concentrations referring to the composition of the present water, which are presented in Table 11.

TABLE 10

Contents of elements obtained with unfiltered (S) and filtered
(F) oils with 11 μm membrane (F) at 40° C.

| | | mg/Kg | | | | | | | | | | |
|---|---|---|---|---|---|---|---|---|---|---|---|---|
| SAMPLES | | Mg | Na | K | Ca | Sr | Ba | Fe | Zn | Al | Si | Chlorine |
| 2017-011077-06 | S | 7.4 | 280 | 11 | 41 | 3.9 | <0.5 | <0.5 | <0.5 | 1.1 | <1 | 554 |
| | F | 8.7 | 270 | 13 | 45 | 4.7 | <0.5 | <0.5 | <0.5 | — | — | 580 |
| 2017-011650-64 | S | <0.5 | 2.4 | <1.0 | <0.5 | <0.5 | <0.5 | <0.5 | <0.5 | — | — | 31 |
| | F | <0.5 | 11 | 1.9 | 2.5 | <0.5 | <0.5 | <0.5 | <0.5 | 1.8 | <1.0 | 28 |
| 2017-017339-92 | S | 9.5 | 350 | 14 | 57 | 4.9 | <0.5 | 2 | <0.5 | <1 | 1.7 | 591 |
| | F | 9.8 | 300 | 17 | 52 | 5.7 | <0.5 | <0.5 | <0.5 | <1.0 | 1 | 610 |
| 2017-017341-07 | S | 1.0 | 120 | 7.4 | 3.5 | <0.5 | <0.5 | <0.5 | <0.5 | <1 | 2.4-7.2 | 183 |
| | F | 1.0 | 120 | 6.6 | 3 | <0.5 | <0.5 | <0.5 | <0.5 | <1 | <1 | 189 |
| 2018-000938-94 | S | 6.3 | 320 | 14 | 39 | 176 | <0.5 | <0.5 | <0.5 | <1 | <1 | 564 |
| | F | 5.4 | 290 | 17 | 38 | 4 | <0.5 | <0.5 | <0.5 | — | — | 592 |
| 2018-007393-10 | S | <0.5 | 26 | <1.0 | 12 | <0.5 | <0.5 | <0.5 | <0.5 | <1.0 | 7.2 | 83 |
| | F | <0.5 | 15 | <1.0 | 7.2 | <0.5 | <0.5 | <0.5 | <0.5 | — | — | 65 |
| 2018-012019-09 | S | 1.1 | 40 | 1.5 | 15 | <0.5 | <0.5 | <0.5 | <0.5 | <1 | 15-28 | 116 |
| | F | 1.1 | 39 | 1.6 | 16 | <0.5 | <0.5 | <0.5 | <0.5 | <1.0 | <1.0 | 125 |
| 2018-012020-42 | S | 1.0 | 39 | 1.6 | 13 | <0.5 | <0.5 | <0.5 | <0.5 | 1.2 | 1 | 109 |
| | F | 0.94 | 33 | <1.0 | 12 | <0.5 | <0.5 | <0.5 | <0.5 | — | — | 115 |
| 2019-029859-64 | S | <0.5 | 2.6 | <1.0 | 1.1 | <0.5 | <0.5 | <0.5 | <0.5 | <1.0 | <1.0 | 35 |
| | F | <0.5 | 7.9 | <1.0 | 2.8 | <0.5 | <0.5 | <0.5 | <0.5 | <1.0 | <1.0 | 42 |

Figure 9:
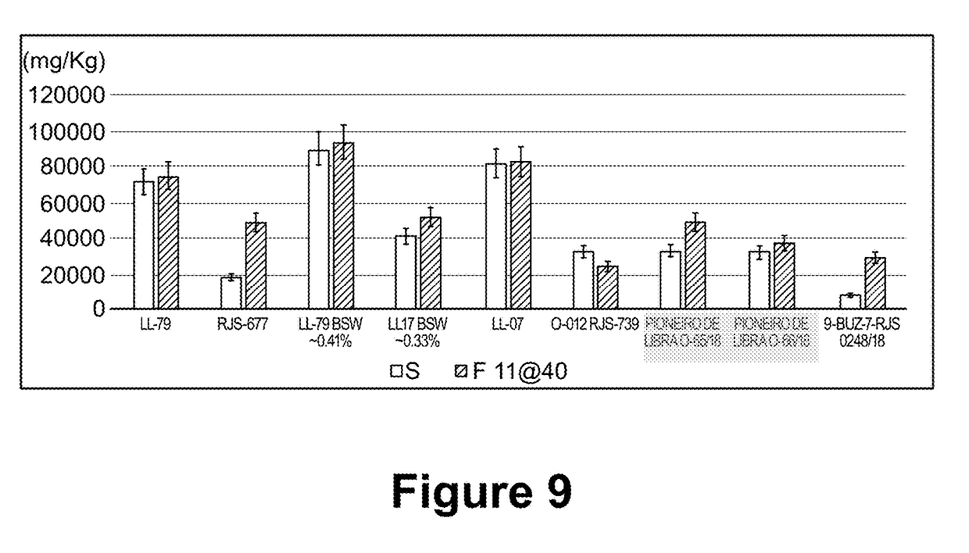
FIG. 9 illustrating a graph of the comparative evaluation of the sodium contents attributed to the water of the unfiltered (S) and filtered (F) oil samples with 11 μm membrane at 40° C.
Figure 10:
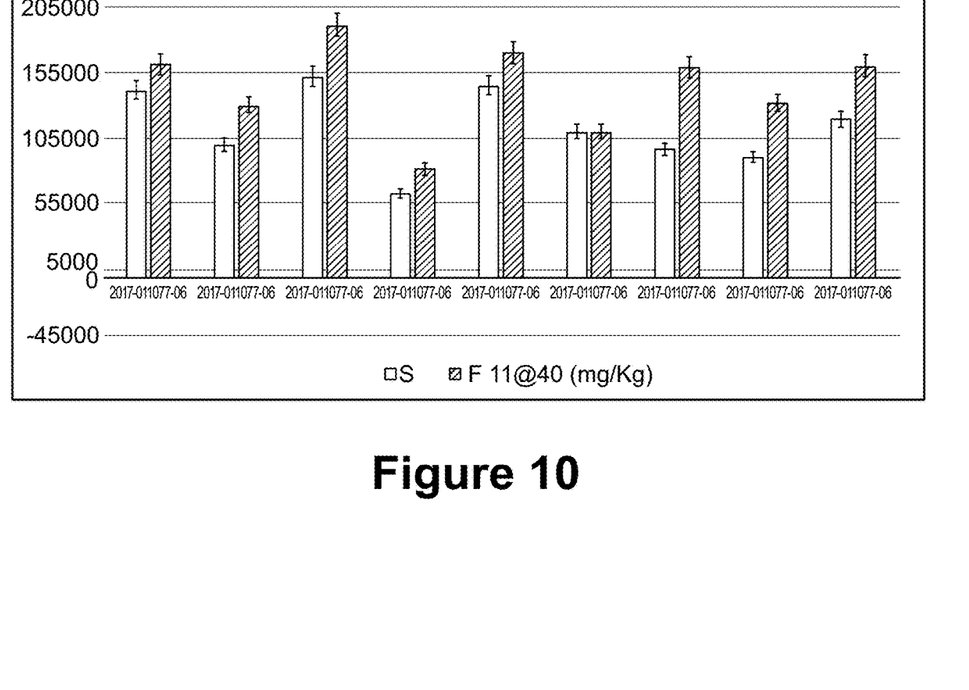
FIG. 10 illustrating a graph of the comparative evaluation of the chloride contents attributed to the water of the unfiltered (S) and filtered (F) samples with 11 μm membrane at 40° C.

The comparison of the results of sodium and chloride contents can be seen in the graphs of FIGS. 9 and 10, respectively.

It can be seen in FIG. 9 that the sodium contents are very regular and very similar to each other, with the exception of the oil samples "2017-011650-64" and "9-2019-029859-64". In these samples, the difference found is related to the low water content, which resulted in high measurement errors due to the low proportion of the present compounds. Therefore, it is considered that, for water contents above 0.1%, the methodology can be applied, whereas for contents below this value it is not recommended to apply the same. Or, in the last case, use only the measurement in the unfiltered sample to have an order of magnitude of the concentration of sodium and chlorine.

When evaluating the chloride content in FIG. 10, it is observed that the results are very constant and practically all the filtered samples showed levels slightly higher than those found in their unfiltered pairs. The only sample that showed a difference that stands out from the others in relation to its unfiltered pair was the oil "2018-012020-42".

The increase in post-filtration chloride concentrations is attributed to the reductions in water concentration promoted by filtration. As the reduction occurred in practically all samples, it is probably related to the performance of the filtration, due to the mild evaporation of the present water, reducing its concentration in the medium.

As the results for chloride and sodium are coherent, it can be considered that the other elements analyzed would also be. Therefore, FIGS. 11 to 14 present the recalculated results

TABLE 11

Results of the calculation of the compounds of interest attributed to water from the
measurements in unfiltered (S) and filtered (F) oils in 11 μm membrane at 40° C.

| | | mg/Kg | | | | | | | | | | |
|---|---|---|---|---|---|---|---|---|---|---|---|---|
| SAMPLES | | Mg | Na | K | Ca | Sr | Ba | Fe | Zn | Al | Si | Cl |
| 2017-011077-06 | S | 1900 | 71800 | 2800 | 10000 | 1000 | <130 | <130 | <130 | 280 | <260 | 142000 |
| | F | 2400 | 75000 | 3600 | 1200 | 1300 | <140 | <140 | <140 | — | — | 161000 |
| 2017-011650-64 | S | <1600 | 18700 | <3300 | <1600 | <1600 | <1600 | <1600 | <1600 | — | — | 100000 |
| | F | <4500 | 49500 | 8600 | 11000 | <2200 | <2200 | <2200 | <2200 | 8100 | <4500 | 130000 |
| 2017-017339-92 | S | 2400 | 90000 | 3600 | 15000 | 1200 | <130 | 500 | <130 | <260 | 440 | 152000 |
| | F | 3100 | 93800 | 5300 | 16000 | 1800 | <156 | <156 | <156 | <313 | 310 | 191000 |
| 2017-017341-07 | S | 340 | 41400 | 2600 | 1200 | <170 | <170 | <170 | <170 | <340 | 830-2500 | 63100 |
| | F | 430 | 52200 | 2900 | 1300 | <220 | <220 | <220 | <220 | <440 | <440 | 82200 |
| 2018-000938-94 | S | 1600 | 82000 | 3600 | 10000 | 45000 | <130 | <130 | <130 | <260 | <260 | 145000 |
| | F | 1500 | 82900 | 4900 | 11000 | 1100 | <140 | <140 | <140 | — | — | 170000 |
| 2018-007393-10 | S | <640 | 32900 | <1280 | 15000 | <640 | <640 | 640 | <640 | <1280 | 9200 | 110000 |
| | F | <830 | 24900 | <1700 | 12000 | <830 | <830 | <830 | <830 | — | — | 110000 |
| 2018-012019-09 | S | 920 | 33300 | 1200 | 1200 | <420 | <420 | <420 | <420 | 830 | 13000-23000 | 96700 |
| | F | 1400 | 49600 | 2000 | 2000 | <640 | <640 | <640 | <640 | <1300 | <1300 | 159000 |
| 2018-012020-42 | S | 830 | 32500 | 1300 | 11000 | <420 | <420 | <420 | <420 | 1000 | 830 | 90800 |
| | F | 1100 | 37900 | <1100 | 14000 | <570 | <570 | <570 | <570 | — | — | 132000 |
| 2019-029859-64 | S | <1700 | 8700 | <3300 | 3700 | <1700 | <1700 | <1700 | <1700 | <3300 | <3300 | 120000 |
| | F | <1900 | 29700 | <3800 | 10000 | <1900 | <1900 | <1900 | <1900 | <3800 | <3800 | 160000 | of the magnesium, potassium, calcium and strontium contents, in that order, attributed to the water.

Figure 11:
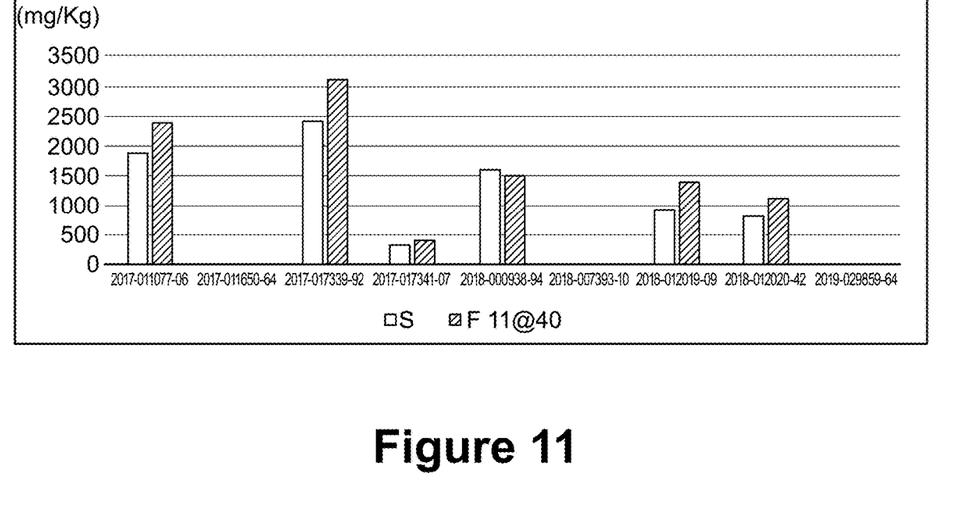
FIG. 11 illustrating a graph of comparative magnesium contents attributed to the water of the unfiltered (S) and filtered (F) samples with 11 μm membrane at 40° C.

The magnesium contents shown in FIG. 11 are very similar to each other, indicating that the filtration did not disturb the medium. The behavior is similar to that of chloride.

Figure 12:
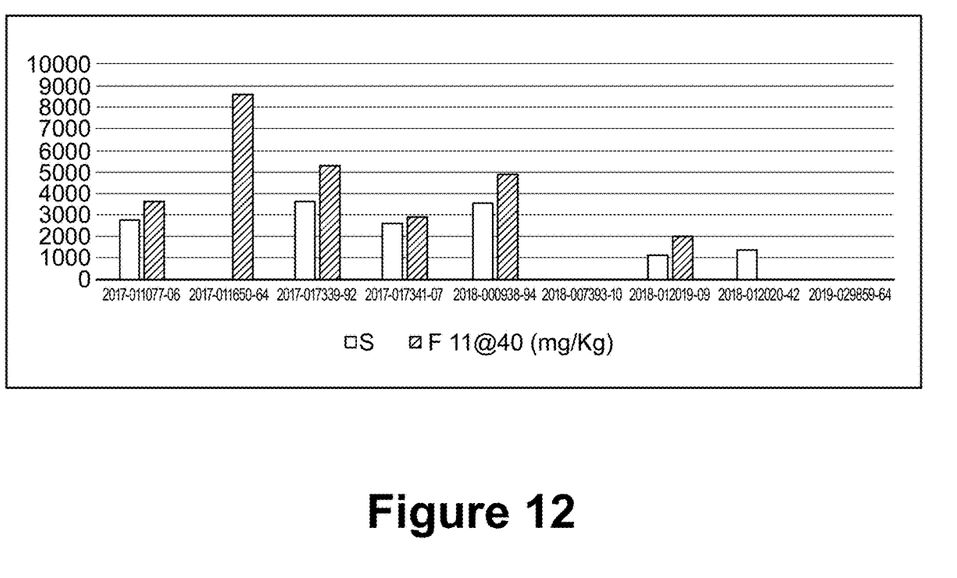
FIG. 12 illustrating a graph of comparative potassium levels attributed to the water of the unfiltered (S) and filtered (F) samples with 11 μm membrane at 40° C.
Figure 13:
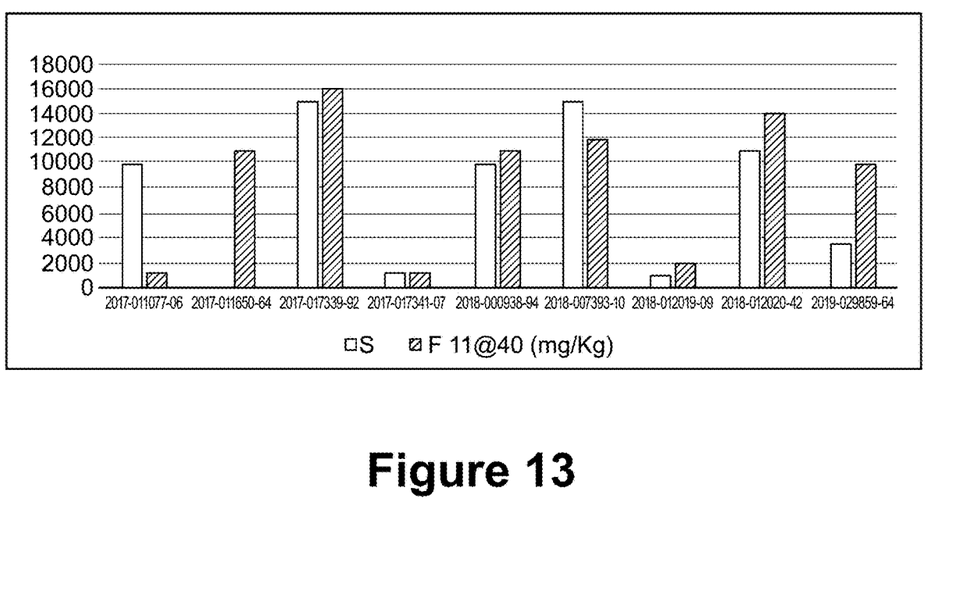
FIG. 13 illustrating a graph of comparative calcium contents attributed to the water of the unfiltered (S) and filtered (F) samples with 11 μm membrane at 40° C.

From FIG. 12, it is observed that two results showed potassium contents only in one of the analyses, an unexpected fact, since it should appear both in the unfiltered and in the filtered ones. These observations are also explained by the low water content of the samples, their values are 305 mg/Kg for the samples of "2017-011650-64" oil and 787 mg/Kg for the "2018-012020-42" oil. These results reinforce the fact that, for samples with water contents below 0.1%, the measurement is compromised.

Sample 2017-011650-64 showed calcium content only for the filtered one, a very unexpected fact; for this compound, it is expected that calcium will be reduced as occurred with the first sample "2017-011077-06" or will not appear in the filtered samples; the reverse should not occur. However, it is observed that the water content in this unfiltered sample is 305 mg/Kg, a value lower than 0.1%. As mentioned, for these cases, the measure considering the developed approach is compromised.

Figure 14:
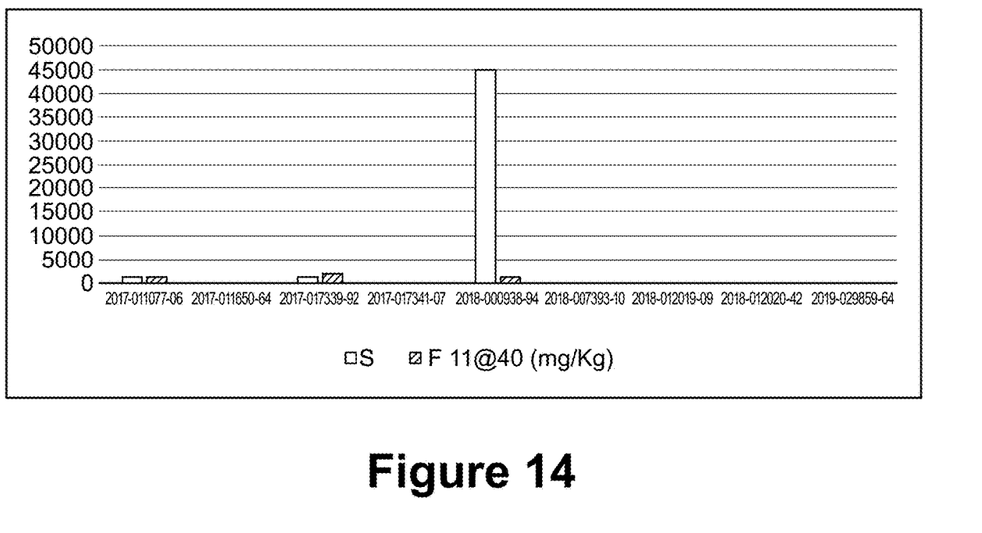
FIG. 14 illustrating a graph of comparative strontium contents attributed to the water of the unfiltered (S) and filtered (F) samples with 11 μm membrane at 40° C.

When evaluating the levels presented in FIG. 14, the presence of a high value of strontium in the unfiltered sample of "2018-000938-94" stands out, and that filtration ensured the removal of the suspended material that contained strontium.

The results obtained denote that the filtration causes the concentrations of the compounds of interest to be a little higher than those found in the samples without filtering, but they do not differ much from the performed measurements. And, at the same time, it was observed that filtration is really necessary as it removes suspended material that would be mistakenly attributed to water. For water contents below 0.1%, filtration should not be applied, for the measurements were compromised for this range.

Example 4: Evaluation of Obtaining an Aqueous Phase with Interference in the Equilibrium In this step, the objective is to obtain the present sulfate content. And to evaluate whether the levels would be consistent, the results of sodium, chloride and potassium were monitored. Leaching was carried out by stirring with turrax for 2 hours, and adding 5 ml of distilled water to 100 ml of filtered oil. After this, a demulsifier was added before and after centrifugation, after which it was stirred for another 5 minutes, and then water was obtained by centrifugation. The water obtained was sent for analysis. The results obtained with the sample "2017-016954-54" are reported in Table 12.

TABLE 12

Results of the characterization of water by leaching of the sample "2017-016954-54".

| Analytes | Content Measured directly in water (mg/L) | Extraction - Final Diss F. - Content in water 5 mL of 100 g of oil (mg/L) | Calculated - Extraction - Final Diss - Content in water 5 mL of 100 g of oil (mg/L) | Extraction - Initial Diss F. - Content in water 5 mL of 100 g of oil (mg/L) | Calculated - Extraction - Initial Diss F. - Content in water 5 mL of 100 g of oil (mg/L) |
|---|---|---|---|---|---|
| Mg | 2400 | 320 | 2130 | 290 | 1933 |
| Na | 71800 | 11300 | 75300 | 7900 | 52667 |
| K | 3200 | 460 | 3100 | 430 | 2867 |
| Ca | 11000 | 1700 | 11000 | 1400 | 9333 |
| Sr | 1200 | 140 | 930 | 130 | 867 |
| Ba | 3.1 | 0.3 | 2.0 | 0.6 | 4.0 |
| Fe | <0.2 | <0.1 | <2 | <0.1 | <2 |
| Zn | <0.2 | <0.1 | <2 | <0.1 | <2 |
| Al | <0.2 | <0.1 | <2 | <0.1 | <2 |
| Si | 9.0 | 8.5 | 57 | 7.6 | 51 |
| Chloride | 140000 | 23000 | 150000 | 20000 | 130000 |
| Sulfate | 300 | 130 | 870 | 150 | 1000 |

It can be seen from Table 12 that the extraction with the addition of the demulsifier at the end was more efficient. The results of the analyzed compounds were very close to those obtained directly in the water.

For sulfate, this did not occur; the washing results were much higher than the actual value measured directly in the water.

The methodology was applied to the sample "2017-017339-92", which does not have integrated water analyzed. The aim was to ascertain if it would really be possible to verify if there was sulfate in the sample. The results are reported in Table 13.

TABLE 13

Results of the characterization of water by leaching of the sample "2017-017339-92"

| Analyte | Content in water directly calculated oil mg/Kg | Content in water directly calculated oil mg/L (*) | Calculated content in water of the filtrate mg/Kg | Calculated content in water of the filtrate mg/L (*) | Extraction - Final Diss F. - Content in water 5 mL and 100 g of oil (mg/L) | Calculated - Extraction - Final Diss - Content in water 5 mL and 100 g of oil (mg/L) | Extraction - Initial Diss F. - Content in water 5 mL and 100 g of oil (mg/L) | Calculated - Extraction - Initial Diss F. - Content in water 5 mL and 100 g of oil (mg/L) |
|---|---|---|---|---|---|---|---|---|
| Mg | 2400 | 2100 | 3100 | 2600 | 280 | 3600 | 180 | 2300 |
| Na | 89700 | 76000 | 93750 | 70000 | 8800 | 110000 | 6900 | 88000 |
| K | 3600 | 3000 | 5313 | 4500 | 500 | 6400 | 300 | 3800 |
| Ca | 15000 | 12000 | 16250 | 14000 | 630 | 8100 | 960 | 12000 |
| Sr | 1200 | 1100 | 1781 | 1500 | 150 | 1900 | 100 | 1300 |
| Ba | <130 | <110 | <160 | <130 | 0.1 | 1.3 | <0.1 | <1 |
| Fe | 510 | 440 | <160 | <130 | <0.1 | <1 | <0.1 | <1 |
| Zn | <130 | <110 | <156 | <130 | <0.1 | <1 | <0.1 | <1 |
| Al | 260 | 220 | <313 | <270 | <0.1 | <1 | <0.1 | <1 |
| Si | 440 | 370 | 310 | 270 | 10.0 | 130 | 6.3 | 81 |
| Chloride | 152000 | 128000 | 191000 | 162000 | 21000 | 270000 | 11000 | 140000 |
| Sulfate | — | — | — | — | 140 | 1900 | 110 | 1400 |

(*) estimated density value used 1.18.

When evaluating Table 13, it is observed that the results were in the same order of magnitude and the most efficient extraction was with the addition of a demulsifier at the end of the homogenization.

By evaluating the two samples, it is observed that the methodology can work well to obtain the sulfate content.

Another proposal to evaluate the sulfate content was by performing the opening of the oil sample and obtaining the sulfate content in the solution obtained by ion chromatography. This procedure was performed on filtered samples and on a sample subjected to successive washings with water (Washed oil) and the results were obtained in duplicate as reported in Table 14.

TABLE 14

Samples subjected to opening and measurements of sulfate contents

| Sample | Mass of sample (g) | Sulfate content in mg/L | Sulfate content in mg/Kg |
|---|---|---|---|
| Filtered Oil 11 μm (1) | 5.0351 | 32.887 | 32.66 |
| Filtered Oil 11 μm (2) | 5.017 | 32.321 | 32.21 |
| Filtered Oil 5 μm (1) | 5.0352 | 32.188 | 31.96 |
| Filtered Oil 5 μm (2) | 5.0820 | 32.423 | 31.90 |
| Filtered Oil 0.45 μm (1) | 5.0204 | 11.937 | 11.89 |
| Filtered Oil 0.45 μm (2) | 5.0593 | 10.990 | 10.86 |
| Filtered Oil 1.2 μm (1) | 5.0205 | 14.044 | 13.99 |
| Filtered Oil 1.2 μm (2) | 5.0160 | 12.173 | 12.13 |
| Washed Oil (1) | 5.0069 | 14.308 | 14.29 |
| Washed Oil (2) | 5.0104 | 17.165 | 17.13 |

It was expected that the filtration results presented in Table 14 would be similar to each other, but this did not occur for filtrations with 0.45 μm and 1.2 μm membranes. With the washed sample, it was expected that all the original water would have been removed, or at least partially removed. This occurred, but the results were similar to those of filtrations with 0.45 μm and 1.2 μm, and in this case, as they were not washed, they should present results close to those of oils filtered with 11 and 5 μm or higher values than washed oil.

These results indicate that this strategy may be interesting because it would take advantage of the water obtained in the opening performed for analysis by ICP for sulfate determination, being one less process.

Example 5: Evaluation of the Equilibrium Interference Aqueous Phase Separation Technique to Evaluate the Presence of Halobenzoic Tracers in BSW Below 0.5%

This step addresses to the washing of oil in this condition of low water content to obtain a minimum amount of water to subject to the evaluation of tracers. A preliminary test was carried out and the generated water was sent for tracer evaluation. In short, the halobenzoic acids are concentrated in a specific cartridge, the tracers are removed with solvent and this extract is subjected to derivatization with BF3. The derivatized material is then analyzed by gas chromatography coupled to high resolution mass spectrometry. The quantification curves for each possible tracer are used to quantify the tracers present.

The required volumes of oil to be subjected to washing are described in Table 15.

TABLE 15

Amount of oil to obtain the equivalent of 100 mL of water.

| % Water in oil | Volume of oil in Liters to obtain the equivalent of 100 mL of water | Amount of water in mL to be obtained in 5 liters of oil |
|---|---|---|
| 0.1 | 100 | 5 |
| 0.2 | 50 | 10 |
| 0.3 | 33 | 15 |
| 0.4 | 25 | 20 |
| 0.5 | 20 | 25 |

It can be seen from Table 15 that the amount of oil needed to be washed is very high; therefore, for the initial test, we chose to wash 5 liters of oil, which corresponds to the amounts of water reported in the third column of the table. It's a high amount of oil, but for a first experiment it was doable, even without obtaining the equivalent of 100 mL of water (value recommended by the method).

In summary, oil filtrations with fiberglass membranes with pores of 0.45, 1.2, 5 and 11 µm at 40° C. did not interfere with the composition of the filtrate, making it possible to apply the procedure for removal of possible particulates present, preferably carrying out filtrations with 11-micron membranes as it is less laborious and obtains the same results as the others.

The methodologies by ICP and MWDFRX used to determine the elements of interest were satisfactorily applied to the studied oils to obtain the composition of the present water. Sodium and chlorine contents were used to monitor and ensure the correct measurement of the other elements. The contents obtained by the methodologies were attributed to the water without difficulties. On the other hand, for levels below 0.1%, the use of the methodology is not recommended due to the low concentrations of elements associated with water.

The evaluation of the sulfate content by washing/leaching proved to be quite adequate, the levels obtained were semi-quantitative.

The evaluation of halo-benzoic acidic type tracers by washing/leaching and subsequent analysis by mass spectrometry is feasible, even if the answer is only qualitative.

It should be noted that, although the present invention has been described in relation to the attached drawings, it may undergo modifications and adaptations by technicians skilled on the subject, depending on the specific situation, but provided that it is within the inventive scope defined herein.

The invention claimed is:

1. A method for determining the composition of water in oils with basic sediment in water (BSW) below 0.5%, characterized in that it comprises the following steps:
    (a) Homogenizing oil samples for at least 30 minutes;
    (b) Filtering the oil samples using a system for pumping under pressure using peristaltic pumps or "pan" system pressurized with $N_2$, under heating at a temperature between 40° C. and 60° C.;
    (c) Determining the water content in the oil samples by volumetric Karl Fischer titration;
    (d) Determining the metals in the oil samples by means of incineration, in which the ashes obtained are mineralized, where the solution obtained is analyzed by the techniques of AAS or ICP-AES; and for the determination of metals in integrated water, the aqueous sample is filtered, diluted between 10 and 20 times, and then this solution is analyzed by ICP-OES;
    (e) Determining the total chlorine content directly in the oil samples using monochromatic wavelength scattering X-ray fluorescence spectroscopy (MWDFRX);
    (f) Performing liquid-liquid extraction with 100 grams of oil sample by adding 5 grams of distilled water, homogenizing the mixture for 2 hours, then adding a demulsifier, and perform a new homogenization for another 5 minutes; then, pouring the oil with the separated water into a separating funnel to obtain the water;
    (g) Determining the chloride content directly in integrated water or in the aqueous extract by potentiometric titration;
    (h) Determining the alkalinity directly in the aqueous extract by titration with acidic solution;
    (i) Performing liquid-liquid extraction for tracer evaluation through 500 mL of oil added to 175 mL of toluene, 50 mL of saline solution (35 g/100 mL) and 10 drops of demulsifier, homogenizing the mixture in a mechanical stirrer for 30 minutes and then subjecting to centrifugation for two hours at 40° C. under rotation of 11000 rpm;
    (j) Performing the analysis of tracers in the aqueous phase obtained in step (i) using extraction by SPE acidification and derivatization to qualify the presence by gas chromatography coupled to high resolution mass spectrometry (GC/HR-MS) or gas chromatography coupled to triple quadrupole mass spectrometry.

2. The method according to claim 1, characterized in that the membranes of the system of step (b) are made of nylon and have a pore diameter of 0.45 µm, 1.2 µm, 5 µm, or 11 µm.

3. The method according to claim 1, characterized in that, in step (d), it determines Si and Al, by melting the ashes, using a specific flux mixture.

4. The method according to claim 1, characterized in that, in step (f), it adds the demulsifier, before the homogenization, and centrifuges the mixture for 30 minutes.

5. The method THE METHOD according to claim 1, characterized in that the potentiometric titration of step (g) is carried out with silver nitrate using a glass electrode containing silver electrode.

6. The method THE METHOD according to claim 1, characterized in that, in the liquid-liquid extraction of step (i), three successive washings are carried out, to obtain water related to the washing of 5 liters of oil and adjust the pH of this water with potassium hydroxide until pH 8.

* * * * *